United States Patent [19]

Goudar

[11] Patent Number: 5,543,541

[45] Date of Patent: Aug. 6, 1996

[54] METHOD OF PREPARING ARYL TRIAZOLINONES WITH TRIALKYL ORTHOACETATES

[75] Inventor: Jaidev S. Goudar, Plainsboro, N.J.

[73] Assignee: FMC Corporation, Philadelphia, Pa.

[21] Appl. No.: 416,560

[22] Filed: Apr. 4, 1995

Related U.S. Application Data

[62] Division of Ser. No. 263,586, Jun. 22, 1994, Pat. No. 5,449,784.

[51] Int. Cl.$^6$ .................................................. C07C 243/22
[52] U.S. Cl. ................................................................ 558/6
[58] Field of Search ........................................... 558/6

[56] References Cited

U.S. PATENT DOCUMENTS

| | | | |
|---|---|---|---|
| 4,818,275 | 4/1989 | Theodoridis | 71/92 |
| 4,980,480 | 12/1990 | Theodoridis | 548/263.2 |
| 5,125,958 | 6/1991 | Poaa | 71/92 |
| 5,256,793 | 10/1993 | Bailey et al. | 548/263.2 |

OTHER PUBLICATIONS

Comptes Rendes (1978), 287(3), 69–72.

*Primary Examiner*—Richard L. Raymond
*Attorney, Agent, or Firm*—Stanford M. Back; Robert M. Kennedy

[57] ABSTRACT

A method for preparing an alkoxyethylidene-substituted aryl hydrazine having the formula

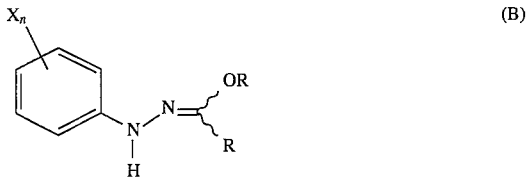

(B)

and thereafter cyclizing the same with a cyanate salt under mildly acidic conditions in the presence of an organic solvent, optionally in the presence of a cyclization-aiding amount of water, to form an aryl triazolinone of the formula

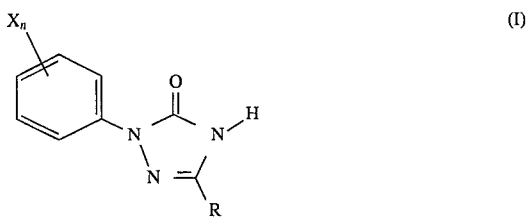

(I)

wherein X is independently hydrogen, halogen, lower alkyl, lower alkoxy, nitro, hydroxy, —NHSO$_2$R$^1$, —NR$^1$SO$_2$R$^1$, or —N(SO$_2$R$^1$)$_2$, where R$^1$ is lower alkyl; R is lower alkyl, and each R is the same; and n is an integer of from 1–3, which triazolinones am useful as intermediates for preparing herbicides.

13 Claims, No Drawings

METHOD OF PREPARING ARYL TRIAZOLINONES WITH TRIALKYL ORTHOACETATES

This application is a division, of application Ser. No. 8/263,586 filed Jun. 22, 1994, now U.S. Pat. No. 5,449,784.

BACKGROUND OF THE INVENTION

This application relates to a process for the preparation of aryl triazolinones. More particularly, it relates to an improved process for the preparation of aryl triazolinones by the reaction of an aryl hydrazine with a trialkyl orthoacetate, followed by cyclizing the resulting alkoxyethylidene-substituted aryl hydrazine with a cyanate salt to form the corresponding triazolinones.

This application further relates to the improved cyclization process per se of the alkoxyethylidene-substituted aryl hydrazines to form the corresponding aryl triazolinone.

The thus-produced aryl triazolinones, for example, 4,5-dihydro-3-methyl-1-phenyl-1, 2,4-triazol-5(1H)-one, are useful as intermediates in the production of known herbicides. See, for example, U.S. Pat. Nos. 4,818,275 and 5,125,958, both of which are incorporated herein by reference, wherein conversion of these triazolinone intermediates to known herbicidal products is fully described. (See, for example, cols. 4 and 5 and 6 et seq. of the former patent, as well as col. 2 et seq. of the latter patent.)

SUMMARY OF THE INVENTION

In accordance with the present invention there is provided an improved process for the production of aryl triazolinones having the formula

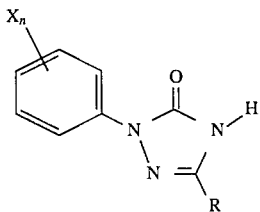

which comprises reacting an aryl hydrazine of the formula

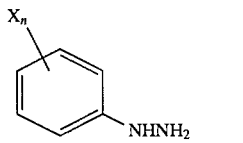

with a tri-lower alkyl orthoacetate, $CH_3C(OR)_3$, in a lower alkanol solvent whose alkyl groups correspond to those of the tri-lower alkyl orthoacetate, optionally in the presence of a catalyst, to form the corresponding aikoxyethylidene-substituted aryl hydrazine having the formula

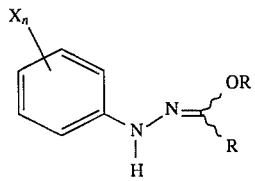

and thereafter cyclizing the alkoxyethylidene-substituted aryl hydrazine with a cyanate salt under mildly acidic conditions in the presence of a lower alkanol solvent, optionally in the presence of a cyclization-aiding amount of water, to form the aryl triazolinone of formula (I);

wherein X is independently hydrogen, halogen, lower alkyl, lower alkoxy, nitro, hydroxy, $—NHSO_2R^1$, $—NR^1SO_2R^1$, or $—N(SO_2R^1)_2$, where $R^1$ is lower alkyl;

R is lower alkyl, and each R is the same; and n is an integer of from 1–3.

A reaction scheme depicting this process is set forth in Table 1, below.

This process, which may be carried out in one continuous two-step manner, or in two separate steps, is advantageous over known routes to aryl triazolinones in that the oxidation step from the aryl triazolidinone to the aryl triazolinone is eliminated (see U.S. Pat. No. 5,256,793), thereby avoiding a potentially dangerous step, which saves time and other process expenditures.

As aforestated, one known method for preparing these aryl triazolinones, and converting them to useful herbicides, is disclosed in U.S. Pat. Nos. 4,818,275, and 5,125,958 (supra). See, also, Comptes Rendus Hebd. Seances Acad. Sci., Ser. C, 1978 287(3), 69–72, which discloses the conversion of aryl hydrazines to the corresponding alkoxyethylidene-substituted aryl hydrazine intermediates.

DETAILED DESCRIPTION OF THE INVENTION

In accordance with the present invention, the aryl hydrazine of formula (A) above (e.g., phenylhydrazine) is reacted with a tri-lower alkyl ortho-acetate, $CH_3C(OR)_3$, wherein each alkyl in the trialkyl moiety is the same and is preferably about one to three carbon atoms in length. Trimethyl orthoacetate (TMOA) is the preferred reactant. A useful ratio of moles of trialkyl orthoacetate to moles of aryl hydrazine (A) is about one to five moles of orthoacetate to one mole of aryl hydrazine; preferably about 1–1.4 to one mole.

The reaction is conducted in a lower alkanol solvent medium wherein the alkanol solvent is preferably about one to three carbon atoms in length, and most preferably is methanol; with the proviso that the trialkyl moiety of the trialkyl orthoacetate and the alkanol solvent must be of the same carbon chain length. For example, to prevent transesterification, the reaction must be conducted in methanol if the aryl hydrazine (A) is reacted with trimethyl orthoacetate. A useful ratio of alkanol solvent to aryl hydrazine (liters/mole) is about 0.5–2 liters of solvent to one mole of aryl hydrazine (A); preferably about 1–1.3 liters to one mole.

The reaction generally proceeds rapidly at a relatively low temperature. Thus, for example, the formation of intermediate (B) is usually complete in from about one to 18 hours at a temperature of from 40° to 100° C., and usually in one to two hours at 40° to 65° C. For example, in 1.5 hours in refluxing methanol, at the latter temperature, there is provided the corresponding intermediate N—aryl—N'—(1-alkoxyethylidene)hydrazine of formula (B) in quantitative yield.

In an alternative method, the reaction can be carded out at a much faster rate and at a lower temperature, for example, in about ten minutes at ambient temperature, if a catalytic amount of a weak protic acid such as formic acid, acetic acid, propanoic acid, p-toluenesulfonic acid or the like, preferably acetic acid, is initially added to the reaction mixture. This alternative procedure, however, requires that the reaction be carefully monitored to prevent an acidcatalyzed polymerization of the N—aryl—N'—(1 alkoxyethylidene) hydrazine (B).

While the thus-prepared intermediate N—aryl—N'—(1-alkoxyethylidene)-hydrazine (B) may optionally be isolated from the reaction mixture, it is preferably cyclized in situ using a cyanate salt such as the cyanate salts of silver, sodium or potassium, of which potassium or sodium cyanate is preferred. A useful ratio of moles of cyanate salt to moles of aryl hydrazine (A) is about one to two moles of cyanate salt to one mole of aryl hydrazine; preferably 1.2–1.4 to one.

To effect cyclization to the aryl triazolinone of formula (I), the reaction must be conducted under mildly acidic conditions, i.e., at pH's of about 3–6, preferably about 4–5, in the presence of a lower alkanol solvent. Otherwise, the use of a strong acid would 1) hydrolyze the N—aryl—N'—(1-alkoxyethylidene)hydrazine (B), affording the aryl hydrazine (A) and methyl acetate, and 2) polymerize the cyanate. Any number of weak protic acids disclosed above, such as, but not limited to, formic acid, acetic propanoic acid or p-toluenesulfonic acid, are useful for cyclization. Acetic acid is the preferred weak protic acid. A useful ratio of moles of weak protic acid to moles of aryl hydrazine (A) is one to two moles of acid to one mole of aryl hydrazine; preferably 1.2–1.4 to one.

Optionally, it has been found that the addition of water to the reaction mixture significantly reduces the time required for completion of cyclization from about 24 hours to about two to ten hours. A useful ratio of volume of cyclization-aiding water to volume of lower alkanol solvent, for example, methanol, is about one volume of water to five to 12 volumes of solvent; preferably about one volume to 7–10 volumes. Thus, for example, the formation of the aryl triazolinone (I), i.e., 4,5-dihydro-3-methyl-1-phenyl- 1,2,4-triazol-5(1H)-one, in 40 to 90% yield, is completed in from about two to 10 hours at a temperature of from 20° to 50° C., preferably at ambient temperature, when the cyclization to the aryl triazolinone (I) is aided by the addition of about one volume of water for each five to 12 volumes of reaction mixture solvent Other solvents which may be employed include N,N-dimethylformamide, dioxane, and tetrahydrofuran.

The aryl triazolinone product (I) may be routinely isolated from the reaction mixture, e.g., by stripping off the solvent, and washed with, for example, hexane, or recrystallized from, for example, toluene, prior to its use as an intermediate in subsequent process steps, as described in the art.

As aforestated, the process of the present invention may advantageously be conducted in one reaction vessel, even though it is a two-step process, in which case the reaction conditions for the second step must be adjusted in a timely fashion. The resultant homogeneous reaction mixture provides a product free from problem-causing by-products. However, one of the by-products formed in the present process is a lower alkanol, e.g., methanol, which can readily be removed from the reaction mixture and reused in other runs of this process.

EXAMPLES

The following examples are provided by way of illustration of the aforedescribed invention, but not by way of limitation.

These examples, and other runs illustrating this process, are summarized in Table 1 which follows the examples.

EXAMPLE 1

SYNTHESIS OF
4,5-DIHYDRO-3-METHYL-1-PHENYL-1,2,4-TRIAZOL-5(1H)-ONE USING TRIMETHYL ORTHOACETATE

A stirred solution of 2.0 grams (0.019 mole) of phenylhydrazine and 11.1 grams (0.092 mole-5 eq.) of trimethyl orthoacetate (TMOA) in 20 mL of methanol was heated at reflux for about six hours. The reaction mixture was then allowed to cool to ambient temperature where it stirred for about 18 hours. The reaction mixture was again warmed to reflux where it stirred for another six hours, until the reaction to the intermediate N—phenyl—N'—(1-methoxyethylidene) hydrazine was complete. The progress of the reaction was monitored by gas chromatograph (GC). After this time, the reaction mixture was cooled in an ice-water bath (0° C.), and 1.5 grams (0.023 mole-1.2 eq.) of sodium cyanate was added. Upon completion of addition, 1.6 grams (0.026 mole-1.4 eq.) of acetic acid was added dropwise. The reaction mixture was then stirred at the ice-water bath temperature for about 10 minutes and then was allowed to warm to ambient temperature. After this time, two mL of water was added to the reaction mixture. Analysis of the reaction mixture by GC showed formation of the targeted compound. One mL of acetic acid was then added to the reaction mixture, followed by the addition of two mL of water. Upon completion of addition, the reaction mixture was stirred at ambient temperature for about 18 hours. The reaction mixture was concentrated under reduced pressure, yielding 2.5 grams (75.9% yield) of 4,5-dihydro-3-methyl-1-phenyl-1,2,4-triazol-5(1H)-one.

EXAMPLE 2

SYNTHESIS OF
4,5-DIHYDRO-1-(2-FLUOROPHENYL)-3-METHYL-1,2,4 -TRIAZOL-5(1H)-ONE USING TRIMETHYL ORTHOACETATE

One gram (0.008 mole) of 2-fluorophenylhydrazine hydrochloride was dissolved in a dilute aqueous solution of potassium carbonate, and the solution was extracted with two 50 mL portions of methylene chloride. The combined extracts containing the free hydrazine and 1.1 grams (0.010 mole-1.3 eq.) of TMOA were dissolved in 10 mL of methanol, and the stirred solution was heated at reflux for one hour to obtain the intermediate N—phenyl—N'—(1 -methoxyethylidene)hydrazine. The progress of the reaction was monitored by GC. The reaction mixture was then cooled to ambient temperature, and 0.8 gram (0.010 mole-1.3 eq.) of potassium cyanate was added. The reaction mixture was cooled in an ice-water bath (0° C.), and 0.6 gram (0.010 mole-1.3 eq.) of acetic acid was added dropwise. The reaction mixture was then allowed to warm to ambient temperature, and one mL of water was added. Upon completion of addition, the reaction mixture was stirred at ambient temperature for about 18 hours. The reaction mixture was concentrated under reduced pressure to a residue. The residue was washed with three 15 mL portions of hexane, yielding about 0.9 gram (57% yield) of 4,5-dihydro-1-(2-fluorophenyl)-3-methyl-1,2-4-triazol-5 (1H)-one.

EXAMPLE 3

SYNTHESIS OF
4,5-DIHYDRO-3-METHYL-1-PHENYL-1,2,4-TRIAZOL-5 (1H)-ONE USING TRIMETHYL ORTHOACETATE

A stirred solution of 2.0 grams (0.019 mole) of phenylhydrazine and 2.7 grams (0.022 mole-1.2 eq.) of TMOA in 20 mL of methanol is heated at reflux for about 1.5 hours, until the reaction to the intermediate N—phenyl—N'—(1-methoxyethylidene)hydrazine is complete. The progress of the reaction is monitored by gas chromatography (GC). After this time, the reaction mixture is cooled in an ice-water bath (0° C.) and 1.5 grams (0.022 mole-1.2 eq.) of sodium cyanate is added. Upon completion of addition, 1.3 grams (0.022 mole-1.2 eq.) of acetic acid is added dropwise. The reaction mixture is then stirred at the ice-water bath temperature for about 10 minutes, then it is allowed to warm to ambient temperature. After this time, two mL of water is added to the reaction mixture. Upon completion of addition, the reaction mixture is stirred at ambient temperature for about ten hours. The reaction mixture is concentrated under reduced pressure, yielding 4,5-dihydro-3-methyl-1-phenyl-1,2,4-triazol-5(1H)-one.

TABLE

In the following runs of Table 1, the reactants and conditions employed were as follows, unless otherwise indicated:

Hydrazine - phenylhydrazine and 2-fluorophenylhydrazine;

TAOA- trimethyl orthoacetate;

Solvent - methanol (both steps);

Catalyst- acetic acid;

Cyanate - sodium cyanate and potassium cyanate;

Acid (protic acid) - acetic acid; and

Cycl. Aid (cyclizing aid) - water

In these runs, Run 2 corresponds to Example 1, while Run 4 corresponds to Example 2. The remaining runs are either comparative, or show varying reactants or conditions for one or both steps.

TABLE 1

Synthesis of Triazolinones using Trialkyl Orthoacetate (TAOA)

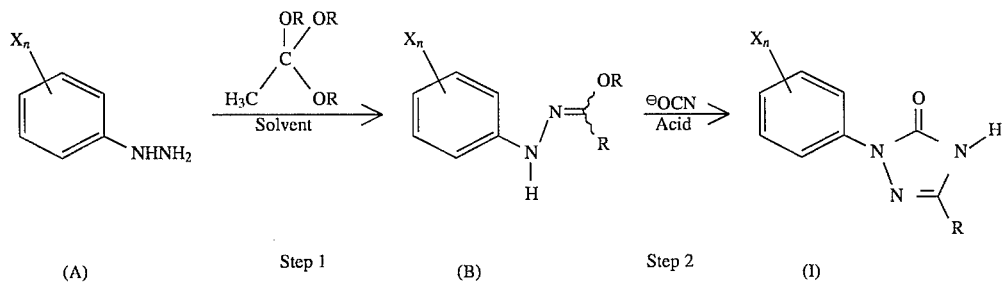

wherein X, R, and n are as defined above.

| | | | Step 1 | | | | | Step 2 | | | | |
|---|---|---|---|---|---|---|---|---|---|---|---|---|
| Run | n | X | Hydrazine (Gm./Mole) | TAOA (Gm./Mole) | Solvent (mL) | Catalyst (Gm.) | Step 1 Rxn. Time/Temp | Cyanate (Gm./Mole) | Acid (Gm./Mole) | Cycl. Aid (mL.) | Step 2 Rxn. Time/Temp | Percent yield |
| 1 | 1 | H | 1.0 0.009 | 1.3 0.011 1.2 eq. | CH₃OH 10 | HOAc 5 drops | Ten min.; Room Temp (RT) | NaOCN 0.7 0.011 | HOAc 0.7 0.011 | — | Time not specified; RT | — |
| Note: HOAc, 5 drops, initially added with hydrazine and TMOA in CH₃OH affording the Step 1 intermediate N-aryl-N'-(1-alkoxyethyl-idene)hydrazine in ~10 min. (Step 1); 0.7 gram (0.011 mole-1.2 eq.) of HOAc added at ~10 min. into rxn. time. Water as a cyclization aid was not used in this experiment. | | | | | | | | | | | | |
| 2 | 1 | H | 2.0 0.019 | 11.1 0.092 ~5 eq. | CH₃OH 20 | — | 12 hr. at reflux and 18 hr. at RT | NaOCN 1.5 0.023 1.2 eq. | HOAc 1.6 0.026 1.4 eq. + *HOAc (1 mL) | Water 4 | ten min at 0° C. and ~18 hr. at RT | 75.9 |
| Note: Hydrazine and TMOA in CH₃OH combined and monitored by gas chromatography (GC) to the formation of the Step 1 intermediate N-aryl-N'-(1-alkoxyethylidene)hydrazine; NaOCN and HOAc were added, followed by * additional amnts. of HOAc, and water. | | | | | | | | | | | | |
| 3 | 1 | H | 0.5 0.005 | 0.8 0.007 1.4 eq. | DMF 5 | — | Time not specified; reflux | * | — | — | Time not specified; reflux | — |
| Note: *Cyanate salt was replaced with 0.5 gram (0.007 mole-1.5 eq.) of methyl carbamate for the Step 2 rxn. DMF solvent was used. | | | | | | | | | | | | |
| 4 | 1 | 2-F | 1.0 0.008 | 1.0 0.010 1.3 eq. | CH₃OH 10 | — | one hr. at rerflux | KOCN 0.8 0.010 | HOAc 0.6 0.010 | Water 1 | ten min at 0° C. and ~18 hr. at RT | 57 |
| Note: 2-fluorophenylhydrazine hydrochloride was used in this rxn. The rxn was conducted in a manner analogous to that of Run. 2 above. | | | | | | | | | | | | |
| 5 | 1 | H | 1.0 0.009 | 1.3 0.011 1.2 eq. | DMF 10 | — | Same as Run 4 | KOCN 0.9 0.011 | HOAc 4.2 0.070 7.8 eq. | Water 1.5 | Same as Run 4 | Trace |
| Note: A large amount of HOAc was used. DMF solvent was used. The rxn was conducted in a manner analogous to that of Runs 2 and 4. | | | | | | | | | | | | |

TABLE 1-continued

Synthesis of Triazolinones using Trialkyl Orthoacetate (TAOA)

| | | | Step 1 | | | | | Step 2 | | | | |
|---|---|---|---|---|---|---|---|---|---|---|---|---|
| Run | n | X | Hydrazine (Gm./Mole) | TAOA (Gm./Mole) | Solvent (mL) | Catalyst (Gm.) | Step 1 Rxn. Time/Temp | Cyanate (Gm./Mole) | Acid (Gm./Mole) | Cycl. Aid (mL.) | Step 2 Rxn. Time/Temp | Percent yield |
| 6 | 1 | H | 1.0 0.009 | 1.3 0.011 1.2 eq. | Dioxane 10 | — | four hrs. at reflux | KOCN 0.9 0.011 | HOAc Amnt. not specified | Water 1 | ten min at 0° C. and ~18 hr. at RT | Trace |

Note: Dioxane solvent used. Dioxane solvent was used. The rxn was conducted in a manner analogous to that of Runs 2 and 4.

| | | | | | | | | | | | | |
|---|---|---|---|---|---|---|---|---|---|---|---|---|
| 7 | 1 | 2-F | 1.0 0.008 | 1.1 0.10 1.3 eq. | CH$_3$OH 10 | — | two hrs. at reflux | KOCN 0.8 0.010 | * | — | ten min at 0° C. and ~18 hr. at RT | ~30 |

Note: 2-fluorophenylhydrazine hydrochloride was used in this rxn. *Acetic acid was replaced with 0.8 gram (0.008 mole-1.0 eq.) of boron trifluoride-methanol complex. The rxn was conducted in a manner analogous to that of Runs. 2 and 4.

I claim:

1. A process for the preparation of an alkoxyethylidene-substituted aryl hydrazine having the formula (B)

which comprises reacting an aryl hydrazine of the formula (A)

with a tri-lower alkyl orthoacetate, CH$_3$C(OR)$_3$, at ambient temperature, in a lower alkanol solvent whose alkyl groups correspond in chain length to those of the tri-lower alkyl orthoacetate, optionally in the presence of a catalyst, to form the corresponding alkoxyethylidene-substituted aryl hydrazine having the formula (B);

wherein X is independently hydrogen, halogen, lower alkyl, lower alkoxy, nitro, hydroxy, —NHSO$_2$R$^1$, or —NR$^1$SO$_2$R$^1$, —N(SO$_2$R$^1$)$_2$, where R$^1$ is lower alkyl;

R is lower alkyl, and each R is the same; and n is an integer of from 1–3.

2. The process according to claim 1 wherein the aryl hydrazine is phenylhydrazine.

3. The process according to claim 1 wherein the aryl hydrazine is 2-fluorophenylhydrazine.

4. The process according to claim 1 wherein R has 1–3 carbon atoms.

5. The process according to claim 1 wherein R is methyl.

6. The process according to claim 1 wherein R$^1$ is methyl.

7. The process according to claim 1 wherein X is —NH—NH$_2$.

8. The process according to claim 1 wherein the lower alkanol solvent employed with the orthoacetate is methanol.

9. The process according to claim 1 wherein the ratio of orthoacetate to hydrazine is about one to five moles of orthoacetate to one mole of hydrazine.

10. The process according to claim 1 wherein the ratio of lower alkanol solvent to hydrazine is about 0.5 to 2 liters of solvent to one mole of hydrazine.

11. The process according to claim 1 wherein a catalyst is present in amounts sufficient to increase the reaction rate and lower the reaction temperature.

12. The process according to claim 11 wherein the catalyst is a weak protic acid.

13. The process according to claim 11 wherein the protic acid is acetic acid.

* * * * *